US009274057B2

(12) United States Patent
Schneider et al.

(10) Patent No.: US 9,274,057 B2
(45) Date of Patent: Mar. 1, 2016

(54) METHOD AND APPARATUS FOR INVESTIGATING A SAMPLE WITH REGARD TO THE LIFETIME OF AN EXCITED STATE

(71) Applicant: Leica Microsystems CMS GmbH, Wetzlar (DE)

(72) Inventors: Juergen Schneider, Sinsheim (DE); Bernd Widzgowski, Dossenheim (DE); Jochen Sieber, Mannheim (DE); Wernher Fouquet, Mannheim (DE); Lars Friedrich, Mannheim (DE); Arnold Giske, Heidelberg (DE); Lioba Kuschel, Mannheim (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 0 days.

(21) Appl. No.: 14/401,952

(22) PCT Filed: Apr. 19, 2013

(86) PCT No.: PCT/EP2013/058195
§ 371 (c)(1),
(2) Date: Nov. 18, 2014

(87) PCT Pub. No.: WO2013/171024
PCT Pub. Date: Nov. 21, 2013

(65) Prior Publication Data
US 2015/0123013 A1 May 7, 2015

(30) Foreign Application Priority Data

May 18, 2012 (DE) .......................... 10 2012 009 780

(51) Int. Cl.
*G01N 21/64* (2006.01)
*G02B 21/00* (2006.01)

(52) U.S. Cl.
CPC ........ *G01N 21/6428* (2013.01); *G01N 21/6408* (2013.01); *G01N 21/6458* (2013.01); *G02B 21/0076* (2013.01); *G01N 2201/06113* (2013.01)

(58) Field of Classification Search
CPC .......... G01N 21/6458; G01N 21/6408; G01N 21/6428
See application file for complete search history.

(56) References Cited

U.S. PATENT DOCUMENTS

2005/0224721 A1* 10/2005 Aoki .......................... 250/458.1
2006/0187448 A1    8/2006 Ye et al.
2008/0024779 A1* 1/2008 Aasmul ........................ 356/317

FOREIGN PATENT DOCUMENTS

DE    102004017956 A1    11/2005
EP        0626575 A1    11/1994

(Continued)

OTHER PUBLICATIONS

Pant et al., "Solvent polarity and viscosity effect on eht fluorescence spectrum and excited state lifetime of quinine dication," 1995, Journal of Photochemistry and Photobiology A: Chemistry, vol. 85, pp. 33-38.*

(Continued)

*Primary Examiner* — Kiho Kim
(74) *Attorney, Agent, or Firm* — Pantentbar International, P.C.

(57) ABSTRACT

The invention relates to a method for investigating a sample with regard to the lifetime of an excited state, in particular a fluorescence lifetime, and/or with regard to a property of a sample which is correlated with a lifetime of an excited state, in particular with a fluorescence lifetime, a sample region being illuminated with a sequence of excitation light pulses. The method is characterized in that the light quantity and/or number of photons of the detected light, in particular fluorescent light, proceeding from the sample region is measured temporally between the excitation light pulses exclusively within a detection time window in each case, at least two detection time windows having different temporal lengths.

20 Claims, 9 Drawing Sheets

(56) References Cited

FOREIGN PATENT DOCUMENTS

| WO | 01/18529 A1 | 3/2001 |
|---|---|---|
| WO | 2011/090745 A1 | 7/2011 |

OTHER PUBLICATIONS

Peon et al., "DNA/RNA nucleotides and nucleosides: direct measurement of escited-state lifetimes by femtosecond fluorescence up-conversion," 2001, Chmical Physics Letters, vol. 348, pp. 255-262.*

International Search Report from PCT/EP2013/058195, filed Apr. 19, 2013, mailed Jul. 8, 2013.

Schwartz et al, "A Single-Photon Avalanche Diode Array for Fluorescence Lifetime Imaging Microscopy," IEEE Journal of Solid-State Circuits, Nov. 2008, pp. 2546-2557, vol. 43, No. 11.

Gerritsen et al, "Fluorescence Lifetime Imaging in Scanning Microscopes: Acquisition Speed, Photon Economy and Lifetime Resolution," Journal of Microscopy, Jun. 2002, pp. 218-224, vol. 206, pt. 3.

Dari-Salisburgo et al, "Laser Induced Fluorescence Instrument for N02 Measurements: Observations at a Central Italy Background Site," Atmospheric Environment, 2009, pp. 970-977, vol. 43.

Lakowicz, "Principles of Fluorescence Spectroscopy," Kluwer Academic/Plenum Publishers, Second Ed., 1999, Chapters 4 & 5.

* cited by examiner a semiconductor laser that emits pulsed excitation light, an adjusting apparatus being provided for adjusting the pulse repetition rate to the specific lifetime properties of the sample.

The electronic system necessary for data evaluation in particular is offered commercially, often in the form of plug-in PC cards. A time-measuring card of this kind is, however, very complex and expensive.

METHOD AND APPARATUS FOR INVESTIGATING A SAMPLE WITH REGARD TO THE LIFETIME OF AN EXCITED STATE

RELATED APPLICATIONS

This Application is a U.S. National Stage Under 35 USC 371 of International Application PCT/EP2013/058195 filed Apr. 19, 2013 which claims priority to a German patent application DE 10 2012 009 780.8, filed May 18, 2012, both of which are incorporated herein by reference in their entirety.

FIELD OF THE INVENTION

The invention relates to a method for investigating a sample with regard to the lifetime of an excited state, in particular a fluorescence lifetime, and/or with regard to a property of a sample which is correlated with a lifetime of an excited state, in particular with a fluorescence lifetime, a sample region being illuminated with a sequence of excitation light pulses; and to an apparatus for executing such a method.

The invention further relates to an apparatus, microscope, in particular scanning microscope, in particular confocal scanning microscope, for investigating a sample with regard to the lifetime of an excited state, in particular a fluorescence lifetime, and/or with regard to a property of a sample which is correlated with a lifetime of an excited state, in particular with a fluorescence lifetime, having a light source that generates a sequence of excitation light pulses in order to illuminate a sample region of a sample.

BACKGROUND OF THE INVENTION

Important knowledge about the properties of a sample can be acquired by investigating the lifetime of the excited states of the sample marked with one or more fluorescent dyes. In particular when multiple fluorescent dyes are used, with the aid of fluorescence lifetime imaging microscopy (FLIM), for example, it is possible to acquire knowledge about a sample region being investigated, for example its composition or environment. In cell biology, for example, the calcium concentration in a sample region can be inferred indirectly by measuring the lifetime of the fluorescent dyes.

FLIM is, in particular, a technique with which the various fluorescence decay times (caused e.g. by the use of various dyes or by different microenvironments) can be depicted as contrast in a microscopic image. Here the fluorescence decay times measured are depicted pixel by pixel, different colors being associated, for example, with pixels having different fluorescence decay times.

There are numerous methods for measuring the lifetime of the excited states of fluorescent dyes. Some of these methods are described in detail in chapters 4 and 5 of the textbook by Joseph R. Lakowicz, "Principles of Fluorescence Spectroscopy," Kluwer Academic/Plenum Publishers, second ed., 1999. For example, it is possible to modulate the power output of the excitation light over time in order to infer, from the phase delay of the emitted light, the lifetime of the excited state.

It is also possible to excite the fluorescent dyes using short light pulses so that the time offset of the emitted light pulses can be measured electronically. DE 10 2004 017 956 A1, for example, discloses a microscope for investigating the lifetime of excited states in a sample, having at least one light source that generates excitation light and having at least one detector that receives the detected light proceeding from the sample. The microscope is characterized in that the light source contains a semiconductor laser that emits pulsed excitation light, an adjusting apparatus being provided for adjusting the pulse repetition rate to the specific lifetime properties of the sample.

The electronic system necessary for data evaluation in particular is offered commercially, often in the form of plug-in PC cards. A time-measuring card of this kind is, however, very complex and expensive.

SUMMARY OF THE INVENTION

The object of the present invention is therefore to describe a method that allows conclusions to be drawn, in a simple manner, with regard to the lifetime of an excited state, in particular a fluorescence lifetime, and/or with regard to a property of a sample which is correlated with a lifetime of an excited state, in particular with a fluorescence lifetime.

This object is achieved by a method which is characterized in that the light quantity and/or number of photons of the detected light, in particular fluorescent light, proceeding from the sample region is measured temporally between the excitation light pulses within a respective detection time window.

A further object of the present invention is to describe an apparatus that can be of simple construction and that allows conclusions to be drawn, in a simple manner, with regard to the lifetime of an excited state, in particular a fluorescence lifetime, and/or with regard to a property of a sample which is correlated with a lifetime of an excited state, in particular with a fluorescence lifetime.

This object is achieved by an apparatus which is characterized in that a detector measures, temporally between the excitation light pulses within a respective detection time window, the light quantity and/or number of photons of the detected light, in particular fluorescent light, proceeding from the sample region.

In a particular embodiment, provision is made that at least two of the detection time windows have different temporal lengths; and/or that at least two detection time windows arranged temporally between different excitation light pulses have different temporal lengths. Provision can be made in particular that a control apparatus modifies the duration of the detection time windows during illumination of a sample region with the sequence of excitation light pulses.

Provision can be made in particular that a detection time window onset of a detection time window is defined by a first time offset from the preceding excitation light pulse; and that a detection time window end is defined by a second time offset from the preceding excitation light pulse.

In an embodiment that can be implemented particularly simply, provision is made that the second time offsets of the detection time windows from the preceding excitation light pulse are identical; and that the first time offset is modified, in particular extended during illumination with the sequence of excitation light pulses in order to generate detection time windows of non-identical lengths.

For execution of the method, it is entirely sufficient if exclusively one single detection time window is provided between each two excitation light pulses.

Provision can be made in particular that each measured light quantity or each number of photons is associated respectively with at least one variable characterizing the pertinent detection time window; and/or that each measured light quantity or each number of photons is associated respectively with the detection time window onset of the respectively pertinent detection time window, in particular if the two offsets of the detection time window from the respectively preceding excitation light pulse are identical. Provision can be made in particular that as a result of the association, a set of n-tuples for further evaluation are formed.

In this manner, the integral over the decay curve is successively sampled. The profile of the decay curve can then be inferred by differentiating over time.

For example, extending the first time offset of the detection time window onset from the respectively preceding excitation light pulse, while second offsets of the detection time window ends from the respectively preceding excitation light pulses remain the same, makes it possible to characterize in simple fashion the decay behavior of an excited state or the excited states of the fluorescent dyes present in the sample region. Because the second time offsets are held constant, each detection time window is completely described by a single variable, namely by the detection time window onset. The result is that the respectively measured light quantity or the respectively measured number of photons needs to be associated with only a single variable, so that by calculating 2-tuples it is possible to record and further evaluate the behavior over time of the sample in the illuminated region as a response to the excitation light pulses.

The set of n-tuples, in particular 2-tuples, constituted as a result of the association can be evaluated, for example using numerical methods, with regard to the lifetime of an excited state, in particular a fluorescence lifetime, and/or with regard to a property of a sample which is correlated with a lifetime of an excited state, in particular with a fluorescence lifetime.

As already mentioned, provision can be made, for example, that in particular in order to ascertain a fluorescence decay curve, the numerical differential over time is calculated from the set of mutually associated tuples. It is also possible firstly to infer from the ascertained tuples the profile of a curve defined by the tuples, and then to differentiate it over time.

Provision can also be made that a decay lifetime and/or a fluorescence half life are ascertained from the set of mutually associated tuples. This can occur, for example, by ascertaining from the data obtained, in particular from the n-tuples, the time intervals within which the number of detected photons has decreased to 1/e or by half.

In particular in order to ensure comparability of the light quantities or numbers of photons detected within the detection time windows, provision is preferably made that the excitation light pulses are identical, in particular in terms of pulse duration and pulse energy; and/or that the time offsets of the excitation light pulses are identical. Apparatuses for regulating the pulse duration and/or for regulating the light power output, which ensure these boundary conditions, can in particular be provided. Alternatively, provision can also be made that fluctuations relating to the properties of the excitation light pulses are measured, and are taken into account upon evaluation in order to correct the data obtained.

An embodiment in which the excitation light pulses are generated with a white light laser, in particular a white light laser that comprises a photonic band gap fiber or a photonic crystal fiber, can be used with particular versatility. This has the advantage that light of the appropriate excitation wavelength can be made available largely for any fluorescent dye. It is of course also possible to apply light of several wavelengths to the sample simultaneously, for example if the sample contains several different fluorescent dyes.

Particularly precise detection of the respective light quantity or number of photons is possible when the detected light is detected with a hybrid detector. Provision can be made in particular that the detected light is detected with a detector that comprises a photocathode downstream from which are placed an electron accelerator and/or an electron multiplier and then an avalanche diode. Such detectors in particular have properties that enable particularly precise execution of the method according to the present invention, namely a large dynamic range, high sensitivity, and a low signal-to-noise ratio.

In a particularly advantageous embodiment, the method is executed using a scanning microscope, in particular a confocal scanning microscope, which for example can comprise a scanning device for directing the excitation light and/or the detected light. It is thereby possible to produce FLIM images of the illuminated sample region and present them to the user on a display.

With regard to the apparatus according to the present invention, a preferably electronic control apparatus can in particular be provided, which apparatus keeps the second offsets of the detection time windows from the preceding excitation light pulse constant and modifies, in particular extends, the first offset, constituting the respective detection time window onset, during illumination with the sequence of excitation light pulses.

Provision can moreover also be made that the control apparatus or an evaluation apparatus associates each measured light quantity or each number of photons respectively with at least one variable characterizing the pertinent detection time window; and/or that the control apparatus associates each measured light quantity or each number of photons respectively with the detection time window onset of the respectively associated detection time window, the latter in particular when the second offsets of the detection time windows from the respectively preceding excitation light pulse are identical.

In particular in order to ascertain a fluorescence decay curve, provision can advantageously be made that the control apparatus or an evaluation apparatus calculates the differential over time and/or the numerical differential over time from the set of mutually associated tuples.

Provision can also be made that the control apparatus or an evaluation apparatus ascertains a decay lifetime and/or a fluorescence half life from the set of mutually associated tuples.

BRIEF DESCRIPTION OF THE DRAWINGS

The invention is schematically depicted in the drawings and will be described below with reference to the drawings; identical or identically functioning elements are usually labeled with the same reference characters. In the drawings.

DETAILED DESCRIPTION OF THE PREFERRED EMBODIMENTS

Figure 1:
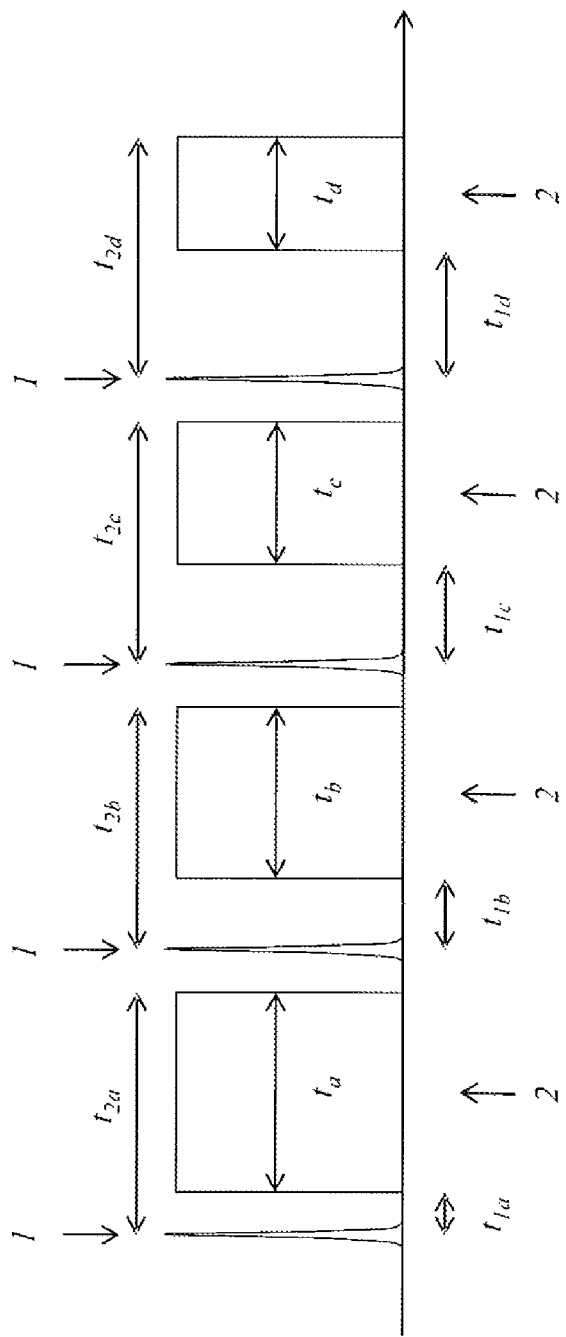
FIG. 1 schematically illustrates the dimensions and arrangement in time of the excitation light pulses and the detection time windows, with reference to an exemplifying embodiment of a method according to the present invention.
Figure 2:
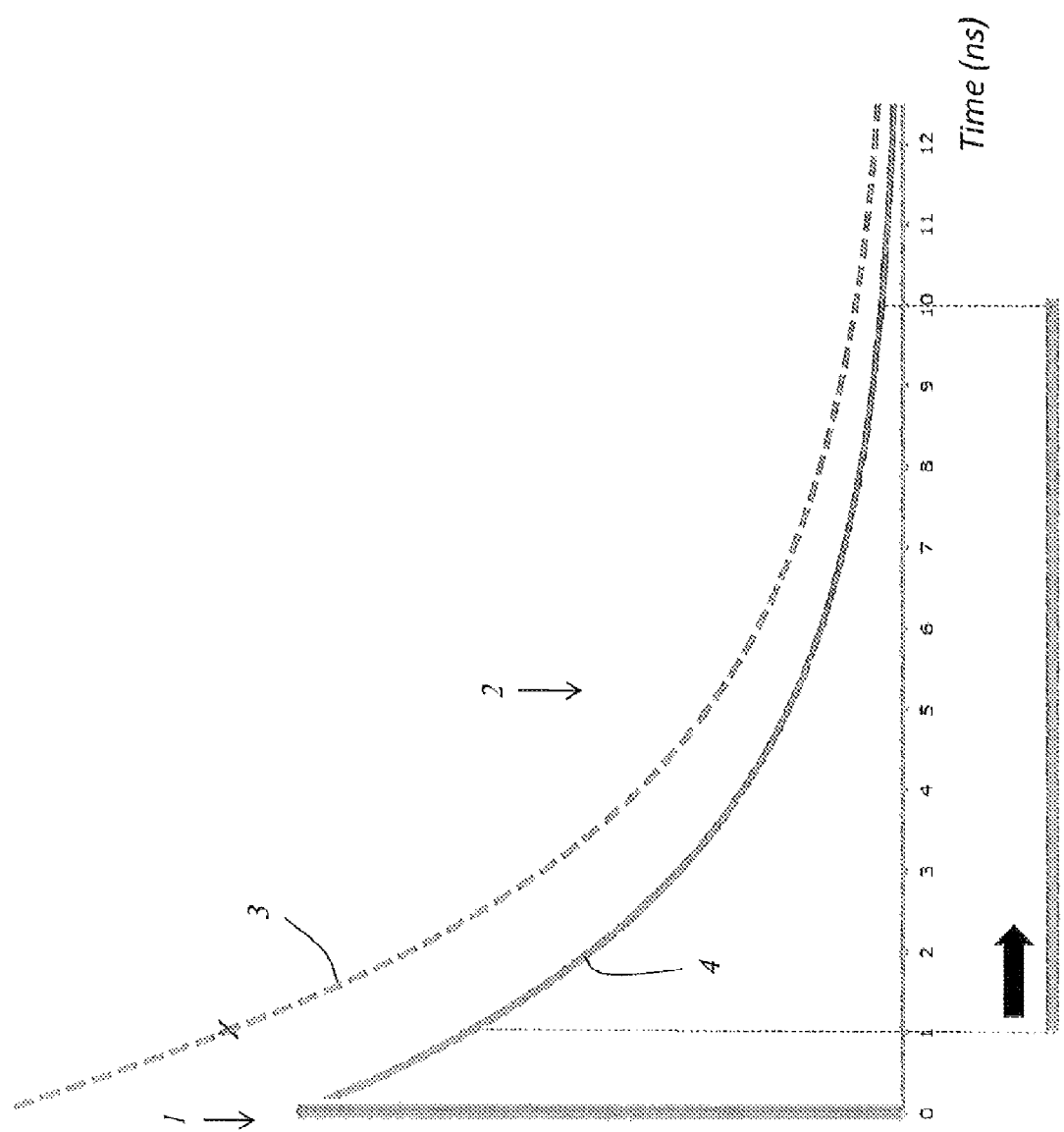
FIGS. 2 to 9 schematically show the principle of measured-value acquisition and data evaluation with reference to an exemplifying embodiment of a method according to the present invention.
Figure 3:
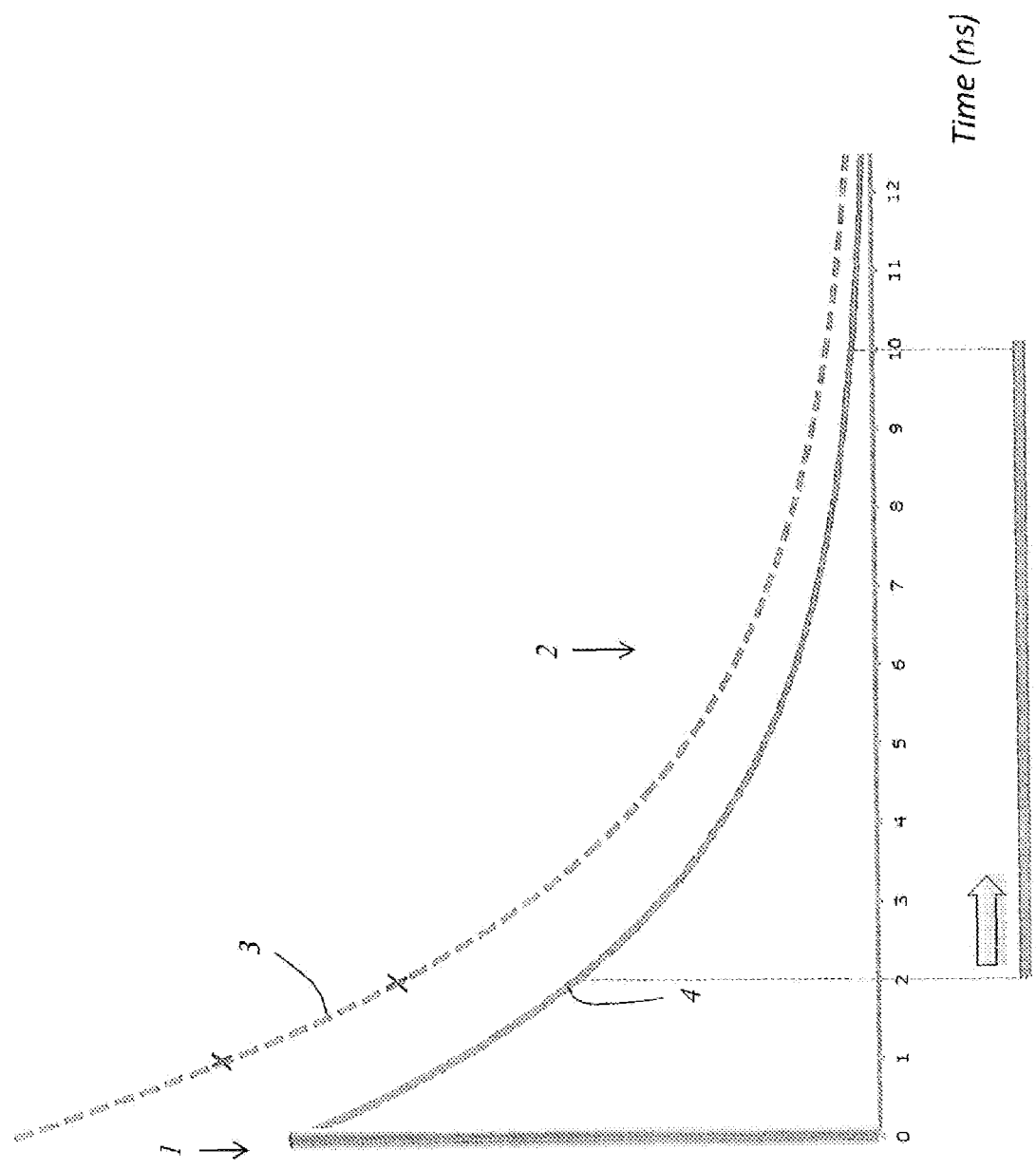
Figure 4:
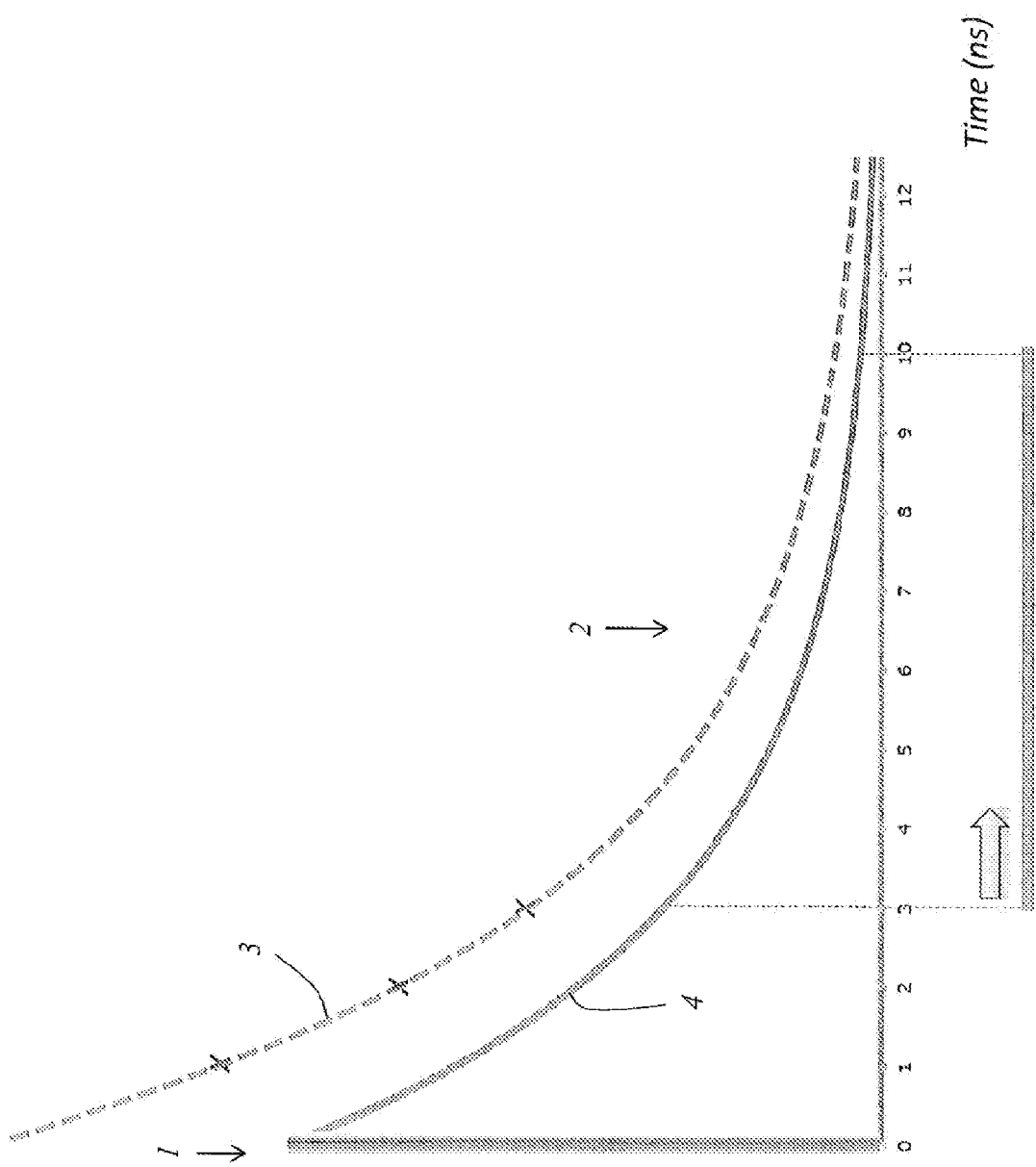
Figure 5:
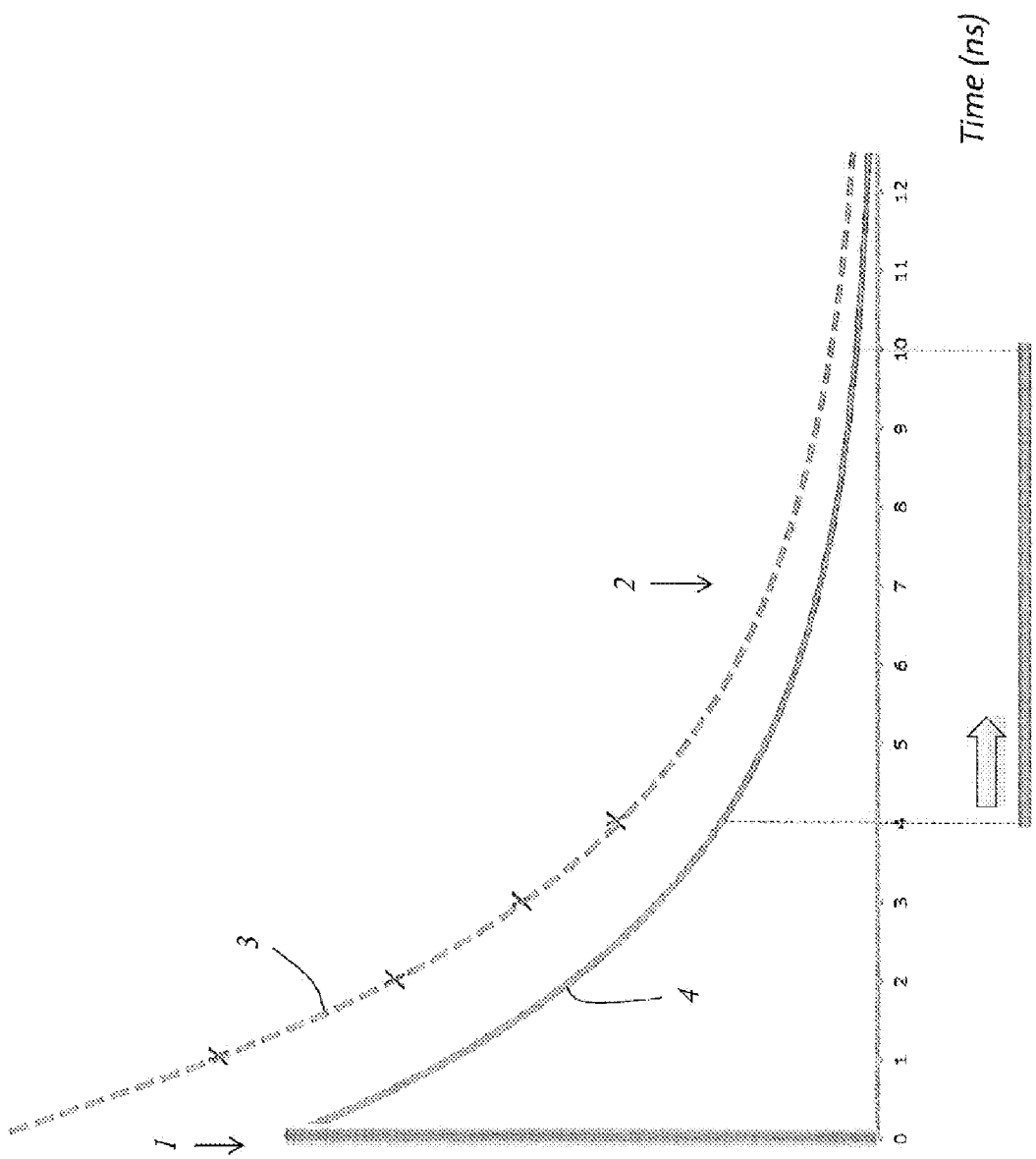
Figure 6:
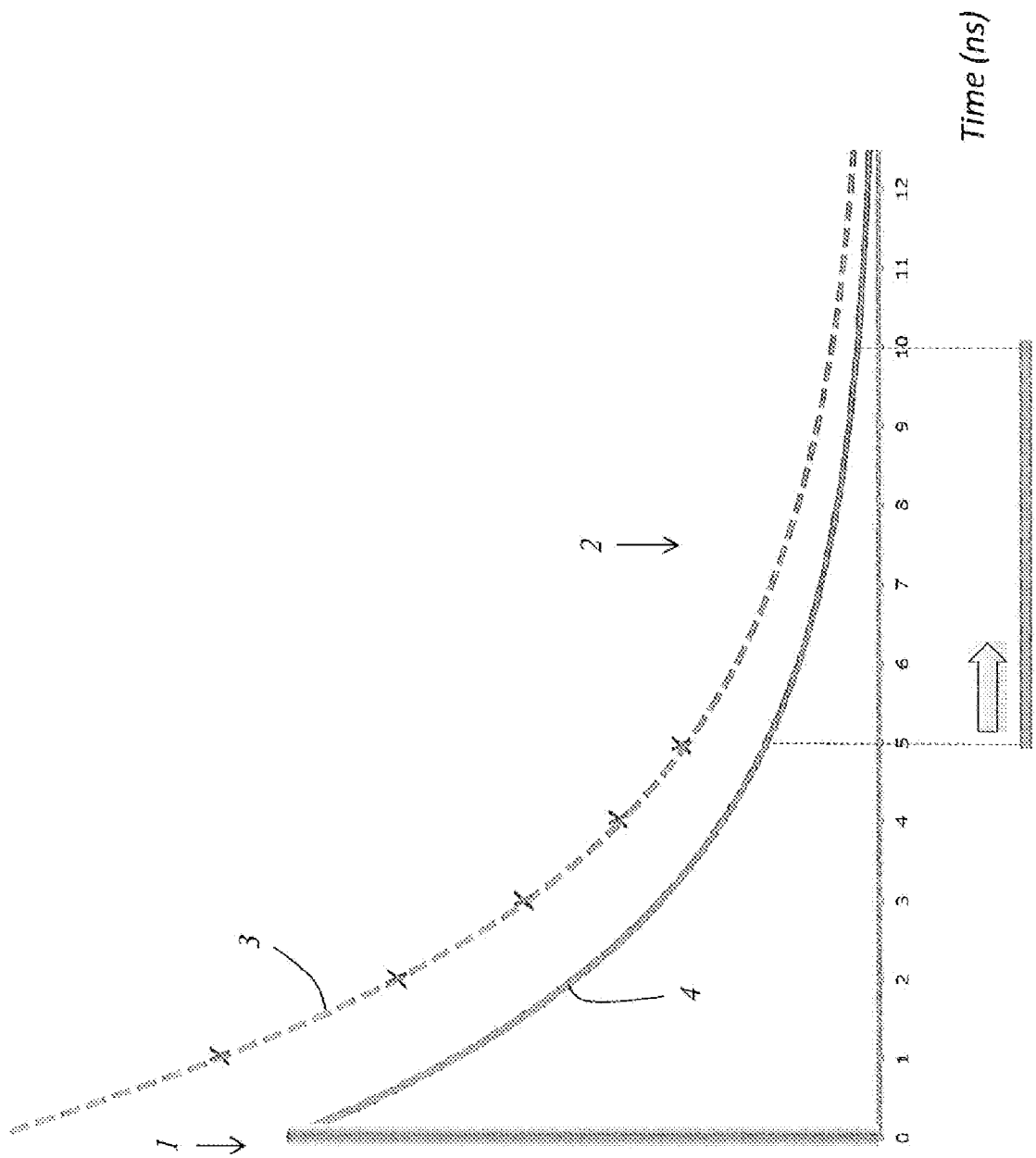
Figure 7:
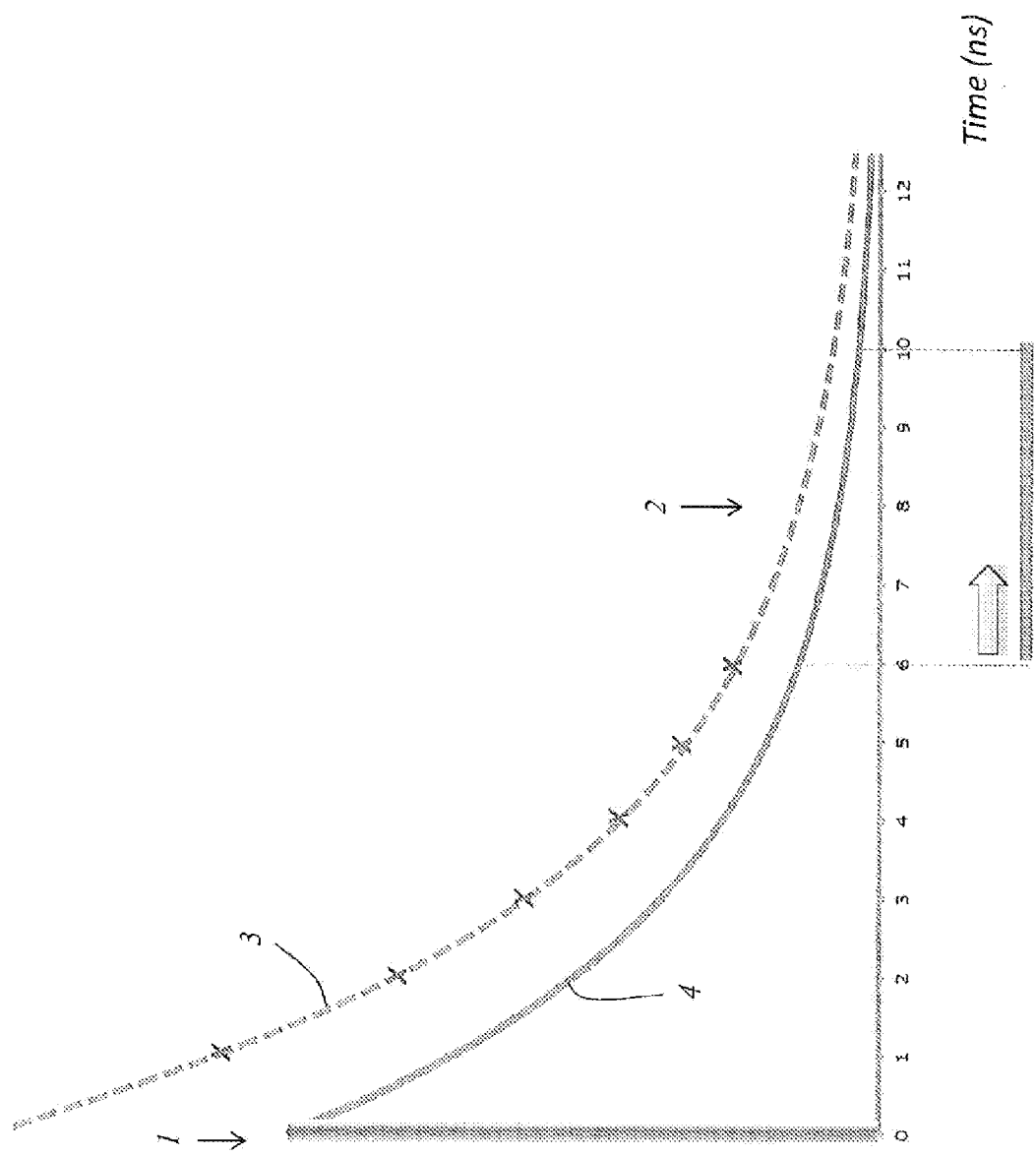
Figure 8:
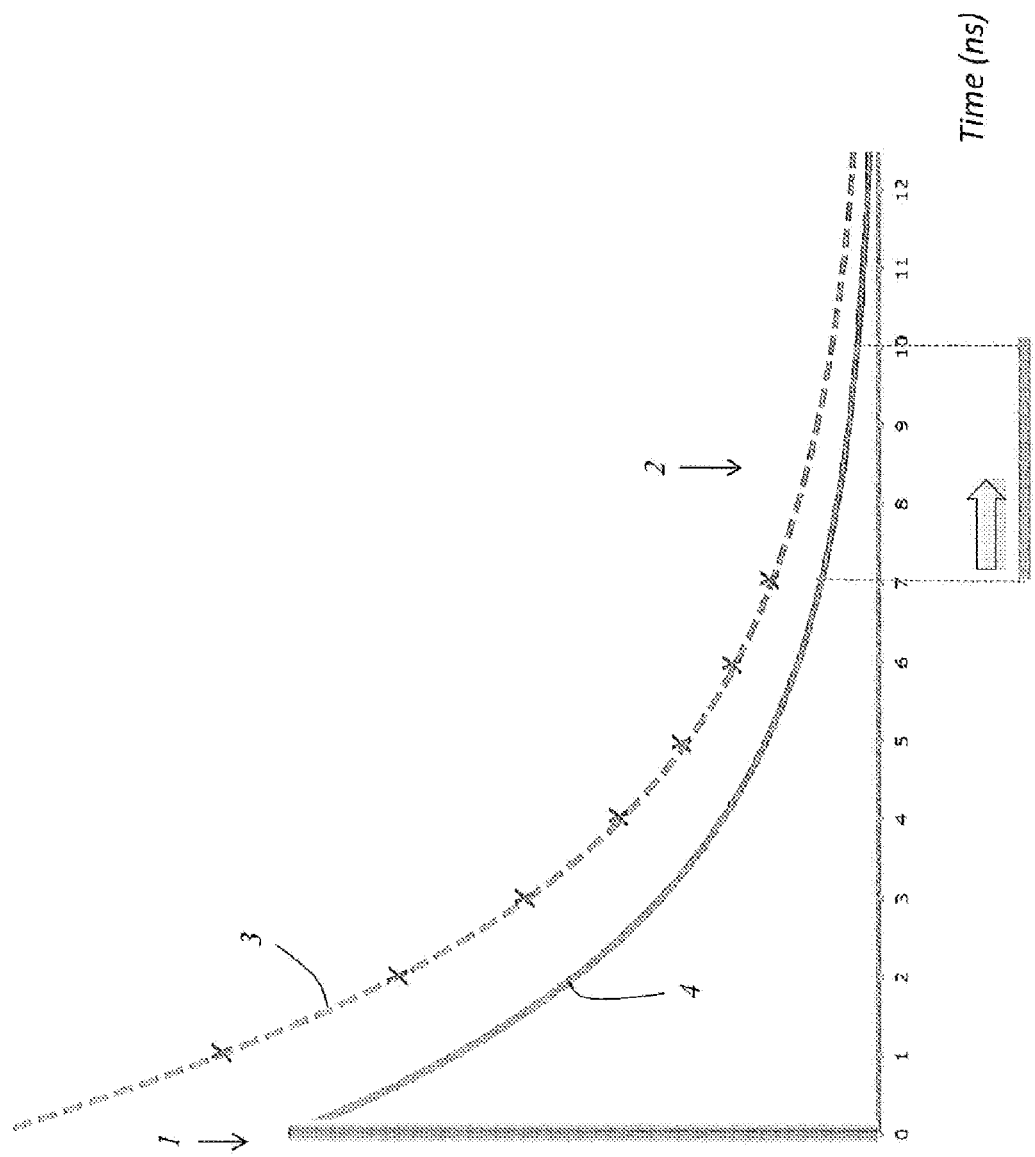
Figure 9:
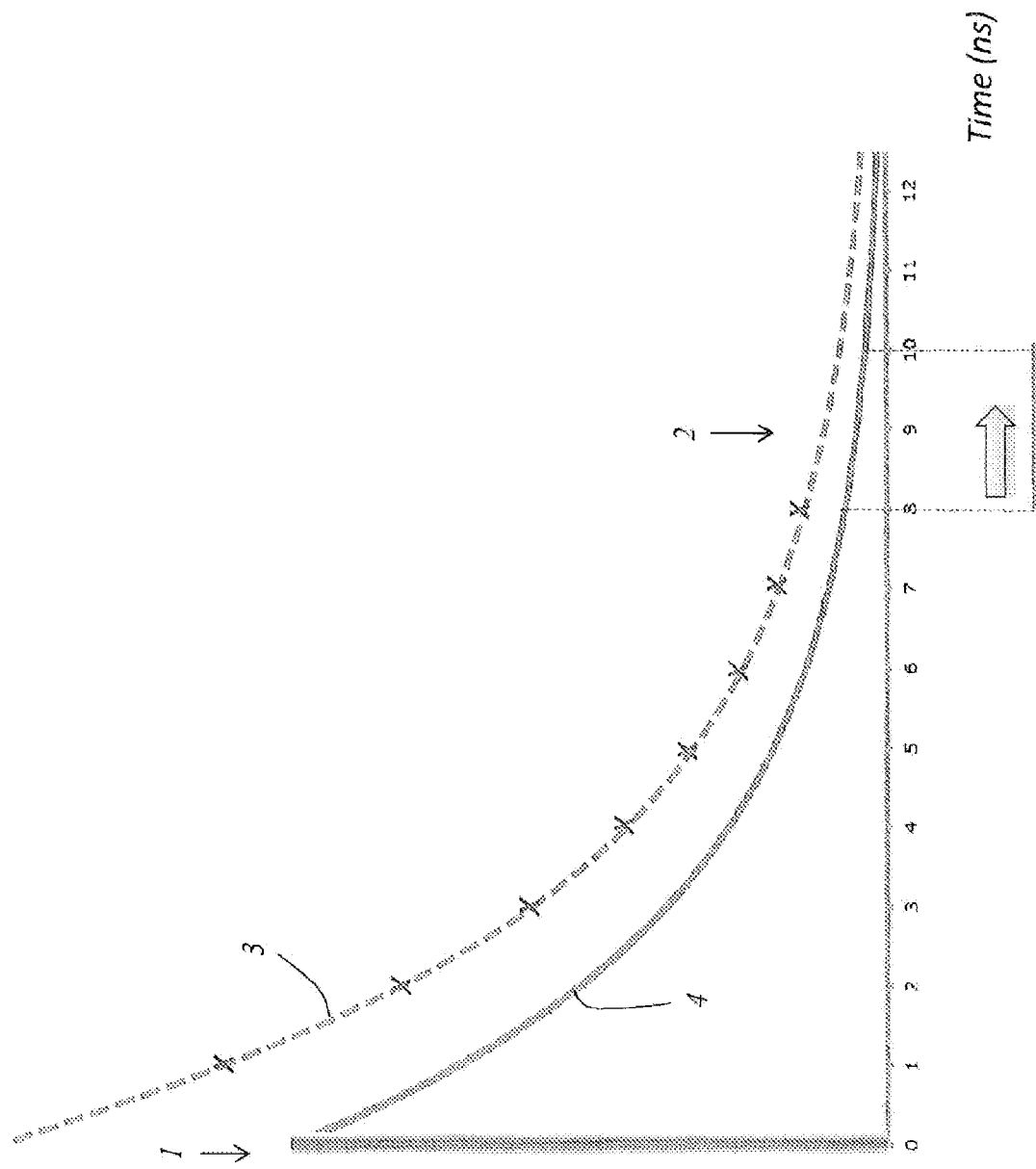

FIG. 1 schematically illustrates the dimensions and arrangement in time of excitation light pulses 1 and detection time windows 2 with reference to an exemplifying embodiment of a method according to the present invention.

Excitation light pulses 1 for illuminating a sample region of a sample, for example with a confocal scanning microscope, are emitted at a constant repetition rate and all have the same pulse duration as well as the sample pulse light output.

The respective light quantity and/or number of photons of the detected light, in particular fluorescent light, proceeding from the sample region is measured in the time between excitation light pulses 1, and in each case exclusively within a detection time window 2 following an excitation light pulse 1, the temporal lengths of detection time windows $t_a$, $t_b$, $t_c$, and $t_d$ being different from one another.

The detection time window onset of a detection time window is defined respectively by a first time offset $t_{1a}$, $t_{1b}$, $t_{1c}$, $t_{1d}$ from the respectively preceding excitation light pulse 1. The detection time window end is defined respectively by a second time offset $t_{2a}$, $t_{2b}$, $t_{2c}$, $t_{2d}$ from the preceding excitation light pulse, the time offsets $t_{2a}$, $t_{2b}$, $t_{2c}$, $t_{2d}$ from the preceding excitation light pulse being, in this exemplifying embodiment, always identical.

During illumination with the sequence of excitation light pulses 1, the first time offset $t_{1a}$, $t_{1b}$, $t_{1c}$, $t_{1d}$ is increasingly extended, and the lengths in time of detection time windows $t_a$, $t_b$, $t_c$, $t_d$ thereby shortened, in order to generate detection time windows 2 of non-identical lengths.

FIGS. 2 to 9 illustrate the manner in which, by measuring the light quantity and/or number of photons of the detected light in each detection time window 2, time integral 3 of fluorescence decay curve 4 is successively sampled, starting from initially long detection time windows 2 (FIG. 2) and transitioning to detection time windows 2 that become increasingly shorter (FIGS. 3 to 9).

Each measured light quantity or each measured number of photons is respectively associated with at least one variable characterizing the pertinent detection time window, namely the respective detection time window onset, and thereby generates 2-tuples of measurement data which are plotted in FIGS. 2 to 9 as crosses on integral curve 3.

The profile of integral curve 3 can be inferred, for example, by interpolation. Fluorescence decay curve 4, and thus the lifetime of an excited state, in particular a fluorescence lifetime, and/or a property of a sample which is correlated with a lifetime of an excited state, in particular with a fluorescence lifetime, can be inferred by numerical differentiation over time using the 2-tuples, or by differentiating the ascertained integral curve 3 over time.

It is possible in particular, with the aid of the measured and/or calculated variables, to generate a FLIM image of a sample region.

The invention has been described with reference to a particular embodiment. It is self-evident, however, that modifications and variants can be effected without thereby departing from the range of protection of the claims that follow.

PARTS LIST

1 Excitation light pulses
2 Detection time windows
3 Integral of fluorescence decay curve 4
4 Fluorescence decay curve
$t_a$, $t_b$, $t_c$, $t_d$ Length in time of detection time window
$t_{1a}$, $t_{1b}$, $t_{1c}$, $t_{1d}$ First time offset
$t_{2a}$, $t_{2b}$, $t_{2c}$, $t_{2d}$ Second time offset

What is claimed is:

1. A method for investigating a sample with regard to a lifetime of an excited state, in particular a fluorescence lifetime, and/or with regard to a property of a sample which is correlated with the lifetime of the excited state, in particular with a fluorescence lifetime, the method comprising:
    illuminating a sample region with a sequence of excitation light pulses; and
    temporally measuring, between the excitation light pulses within a respective detection time window, a light quantity and/or a number of photons of detected light, in particular fluorescent light, proceeding from the sample region,
    wherein a detection time window onset is defined by a first time offset from a preceding excitation light pulse, and a detection time window end is defined by a second time offset from the preceding excitation light pulse,
    wherein, for respective detection time windows from preceding excitation light pulses, second time offsets are identical and first time offsets are modified, in particular extended during illumination with the sequence of excitation light pulses in order to generate detection time windows of non-identical lengths.

2. The method according to claim 1, wherein
    a) at least two detection time windows have different temporal lengths; and/or
    b) at least two detection time windows arranged temporally between different excitation light pulses have different temporal lengths.

3. The method according to claim 1, wherein exclusively one single detection time window is provided between each two excitation light pulses.

4. The method according to claim 1, wherein
    a) each measured light quantity or each number of photons is associated respectively with at least one variable, in particular a time variable, characterizing a respectively pertinent detection time window; and/or
    b) each measured light quantity or each number of photons is associated respectively with the detection time window onset of the respectively pertinent detection time window, in particular if the first time offset and the second time offset of the detection time window from a respectively preceding excitation light pulse are identical.

5. The method according to claim 4, wherein in order to ascertain a fluorescence decay curve, a differential over time and/or a numerical differential over time is calculated from a set of mutually associated tuples.

6. The method according to claim 5, wherein a decay lifetime and/or a fluorescence half life are ascertained from the set of mutually associated tuples.

7. The method according to claim 1, wherein the excitation light pulses are identical, in particular in terms of pulse duration and pulse energy; and/or the first and second time offsets of the excitation light pulses are identical.

8. The method according to claim 1, wherein the excitation light pulses are generated with a white light laser, in particular a white light laser that comprises a photonic band gap fiber or a photonic crystal fiber.

9. The method according to claim 1, wherein
    a) the detected light is detected with a hybrid detector; and/or
    b) the detected light is detected with a detector that comprises a photocathode downstream from which are placed an electron accelerator and/or an electron multiplier and then an avalanche diode.

10. The method according to claim 1, wherein a scanning device for directing the excitation light and/or the detected light is used.

11. The method according to claim 1, wherein a FLIM image of the sample region is generated.

12. An apparatus, microscope, in particular a scanning or confocal scanning microscope, for executing a method according to claim 1.

13. A microscope, in particular a scanning or confocal scanning microscope, for investigating a sample with regard to a lifetime of an excited state, in particular a fluorescence lifetime, and/or with regard to a property of a sample which is correlated with the lifetime of the excited state, in particular with a fluorescence lifetime, having a light source that generates a sequence of excitation light pulses in order to illuminate a sample region of the sample, the microscope comprising:

a detector to measure, temporally between the excitation light pulses within a respective detection time window, a light quantity and/or a number of photons of detected light, in particular fluorescent light, proceeding from the sample region; and a control apparatus to modify a duration of each respective detection time window during illumination of the sample region with the sequence of excitation light pulses, wherein a detection time window onset is defined by a first time offset from a preceding excitation light pulse, and a detection time window end is defined by a second time offset from the preceding excitation light pulse, and second time offsets of detection time windows from preceding excitation light pulses are identical, and during illumination with the sequence of excitation light pulses the control apparatus modifies, in particular extends the first offsets of respective preceding excitation light pulses.

14. The apparatus according to claim 13, wherein a) the control apparatus or an evaluation apparatus associates each measured light quantity or each number of photons respectively with at least one variable characterizing the respectively pertinent detection time window; and/or b) the control apparatus or an evaluation apparatus associates each measured light quantity or each number of photons respectively with the detection time window onset of the respectively associated detection time window, in particular when the second offsets of the detection time windows from the respectively preceding excitation light pulse are identical.

15. The apparatus according to claim 14, wherein in particular in order to ascertain a fluorescence decay curve, the control apparatus or an evaluation apparatus calculates a differential over time and/or a numerical differential over time from a set of mutually associated tuples.

16. The apparatus according to claim 15, wherein the control apparatus or an evaluation apparatus ascertains a decay lifetime and/or a fluorescence half life from the set of mutually associated tuples.

17. The apparatus according to claim 13, wherein the excitation light pulses are identical, in particular in terms of pulse duration and pulse energy; and/or the first and second time offsets of the excitation light pulses are identical.

18. The apparatus according to claim 13, wherein the light source comprises a white light laser; and/or the light source comprises a photonic band gap fiber or a photonic crystal fiber.

19. The method according to claim 13, wherein the detector is embodied as a hybrid detector; and/or the detector comprises a photocathode downstream from which are placed an electron accelerator and/or an electron multiplier and then an avalanche diode.

20. The apparatus according to claim 13, wherein an evaluation apparatus generates a FLIM image of the illuminated sample region.

* * * * *